(12) United States Patent
Morokawa et al.

(10) Patent No.: US 7,625,342 B2
(45) Date of Patent: Dec. 1, 2009

(54) ULTRASONIC ENDOCAVITY PROBE HAVING ADJUSTABLE LENGTH INSERT

(75) Inventors: Tetsuya Morokawa, Tochigi-ken (JP); Yutaka Oonuki, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1073 days.

(21) Appl. No.: 10/813,007

(22) Filed: Mar. 31, 2004

(65) Prior Publication Data
US 2004/0249286 A1 Dec. 9, 2004

(30) Foreign Application Priority Data
Mar. 31, 2003 (JP) ............................. 2003-093879

(51) Int. Cl.
*A61B 8/14* (2006.01)
(52) U.S. Cl. ........................ 600/459; 600/443
(58) Field of Classification Search ................ 600/459, 600/444, 437, 443; 601/3; 411/510, 512, 411/278, 280; 403/107
See application file for complete search history.

(56) References Cited

U.S. PATENT DOCUMENTS

| | | | | |
|---|---|---|---|---|
| 4,930,512 A | * | 6/1990 | Henriksen et al. | 600/452 |
| 5,046,364 A | * | 9/1991 | Stasuk et al. | 73/623 |
| 5,112,339 A | * | 5/1992 | Zelman | 606/107 |
| 5,125,411 A | * | 6/1992 | Yokoi et al. | 600/463 |
| 5,255,669 A | * | 10/1993 | Kubota et al. | 601/3 |
| 5,421,338 A | * | 6/1995 | Crowley et al. | 600/463 |
| 5,674,218 A | * | 10/1997 | Rubinsky et al. | 606/20 |
| 5,674,233 A | * | 10/1997 | Dybbs | 606/166 |
| 5,681,263 A | * | 10/1997 | Flesch | 600/141 |
| 5,762,066 A | * | 6/1998 | Law et al. | 600/439 |
| 5,836,897 A | * | 11/1998 | Sakurai et al. | 601/2 |
| 6,013,030 A | * | 1/2000 | Webler et al. | 600/437 |
| 6,071,238 A | * | 6/2000 | Chapelon et al. | 600/439 |
| 6,248,074 B1 | * | 6/2001 | Ohno et al. | 600/463 |
| 6,364,840 B1 | * | 4/2002 | Crowley | 600/463 |
| 6,537,198 B1 | * | 3/2003 | Vidlund et al. | 600/16 |
| 6,551,245 B1 | * | 4/2003 | Irioka et al. | 600/444 |
| 6,709,397 B2 | * | 3/2004 | Taylor | 600/459 |
| 6,716,184 B2 | * | 4/2004 | Vaezy et al. | 601/3 |
| 7,066,889 B2 | * | 6/2006 | Taylor | 600/459 |
| 7,131,983 B2 | * | 11/2006 | Murakami | 606/169 |

\* cited by examiner

*Primary Examiner*—Eric F Winakur
*Assistant Examiner*—Lawrence N Laryea
(74) *Attorney, Agent, or Firm*—Oblon, Spivak, McClelland, Maier & Neustadt, P.C.

(57) ABSTRACT

An ultrasonic probe for examining a specimen. The ultrasonic probe includes a holding portion, an insertion member, and an ultrasonic generator. The holding portion includes a first housing portion. The insertion member is configured to move along the first housing portion. The insertion member has at least one end for insertion into an endocavity of the specimen. The ultrasonic generator is provided at the one end of the insertion member and configured to transmit an ultrasound pulse to the specimen and collect an echo signal resulting from the transmitted ultrasound pulse.

9 Claims, 8 Drawing Sheets

ULTRASONIC ENDOCAVITY PROBE HAVING ADJUSTABLE LENGTH INSERT

CROSS-REFERENCE TO RELATED APPLICATION

This application is based upon and claims the benefit of priority from prior Japanese Patent Application No. P2003-93879, filed on Mar. 31, 2003, the entire content of which is incorporated herein by reference.

BACKGROUND OF THE INVENTION

1. Field of the Invention

The present invention relates to an ultrasonic probe for obtaining ultrasound images by scanning endocavities of a patient. The present invention also relates to an ultrasound imaging apparatus including an ultrasonic probe.

2. Discussion of the Background

An ultrasound imaging apparatus is well known to be used for medical purposes. The ultrasound imaging apparatus repeats ultrasound pulse transmission by transducers provided in an ultrasonic probe to a body of a patient. The transmitted ultrasound returns to the transducers as ultrasound echo signals. By changing the transmission direction of the ultrasound pulse, ultrasound images are obtained based on ultrasound echo signals collected from a plurality of directions in the body.

As disclosed in Japanese Patent Application Publication No. P2001-178728, one type of the ultrasound imaging apparatus is an ultrasound diagnosis apparatus having an ultrasonic probe which is used in an endocavity of a patient. Such an ultrasonic probe is called an endocavity probe and is used for examinations for, for example, the oral cavity, the endorectal cavity, and the abdominal cavity.

Figure 1:
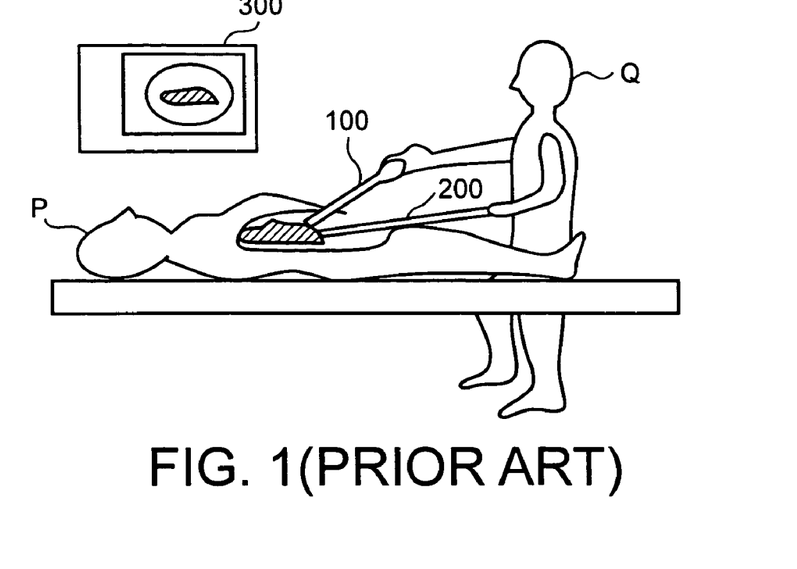
FIG. 1 is an illustration showing a known laparoscopic examination.

FIG. 1 is an illustration showing a known laparoscopic examination.

As shown in FIG. 1, when an ultrasonic probe is used in the laparoscopic examination, an endocavity probe 100 is inserted into the abdominal cavity through one of a plurality of trocars punctured into the abdominal cavity of a patient P. The endocavity probe 100 is handled by an operator Q. The operator Q also handles an endoscope 200 inserted into the abdominal cavity of the patient P through another trocar. The operator Q handles the endoscope 200, observing images obtained by the endoscope 200 and displayed in a display 300, so as to obtain images of a desired part of the patient P. The operator Q handles the endocavity probe 100 and contacts transducers of the endocavity probe 100 with a part in the abdominal cavity so as to obtain ultrasound images including a target part such as a tumor, as examining the abdominal cavity through the endoscope display.

Figure 2:
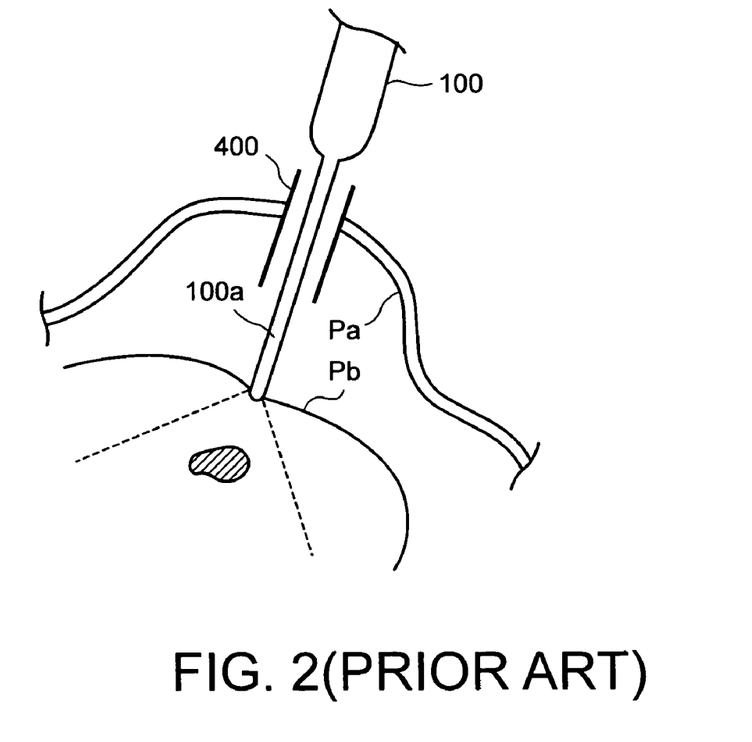
FIG. 2 is an illustration showing one exemplary case of using an endocavity probe in the laparoscopic examination shown in FIG. 1.

FIG. 2 is an illustration showing one exemplary case of using the endocavity probe 100 in the laparoscopic examination shown in FIG. 1. FIG. 2 shows a case that the endocavity probe 100 is used in a laparoscopy with, for example, an aeroperitoneum or a gasless laparolift technique (or an abdominal wall lift technique). In a typical aeroperitoneum, carbon dioxide gas or physiological saline is injected into the abdominal cavity through the trocar 400 so as to create a certain space in the abdominal cavity between an abdominal wall Pa and an organ Pb, such as, for example, a liver. Alternatively, in a typical gasless laparolift technique, the abdominal wall Pa may be mechanically lifted up so as to create a certain space. After the space has been provided, an insertion rod 100a of the above-described endocavity probe 100 is inserted into the abdominal cavity.

Since the abdominal wall is lifted up, the insertion rod 100a is required to have a sufficient length. Therefore, the insertion rod 100a typically has a length (e.g., 300-400 millimeters) enough to reach the organ Pb when the abdominal wall Pa is lifted up and also to scan difficult parts of the organ Pb.

Figure 3:
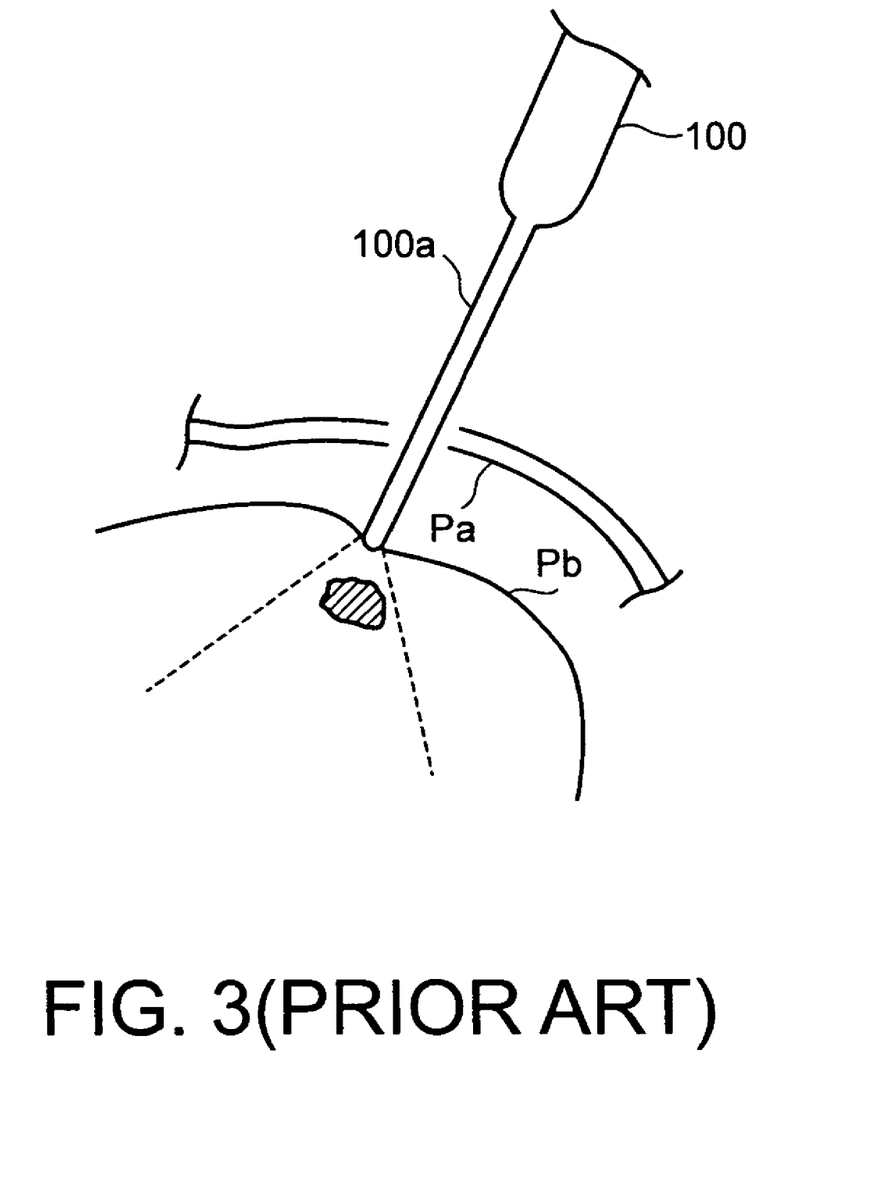
FIG. 3 is an illustration showing another exemplary case of using an endocavity probe in the laparoscopic examination shown in FIG. 1.

In some cases, however, the insertion rod 100a is too long and it may become difficult for the operator Q to handle the endocavity probe 100. That is, the length of the insertion rod 100a in FIG. 2 may result in handling problems of the endocavity probe 100 in some cases. One example case is when the endocavity probe 100 is used for an organ (or any other tissues) at a shallow part from the abdominal wall Pa. The handling problems also depend on the body of the patient P. Another example is a case that the abdominal wall 100a is not lifted up, as shown in FIG. 3. In other words, none of the carbon dioxide gases, the physiological saline, and the mechanical lift-up may be used in an examination with the endocavity probe 100. The trocar may not be used, either. In these cases, the distance between the abdominal wall Pa and the organ Pb is not as long as when the abdominal wall Pa is lifted up. As a result, the insertion rod 100a applied in FIG. 2 becomes too long to handle for the case shown in FIG. 3.

SUMMARY OF THE INVENTION

According to the first aspect of the present invention, there is provided an ultrasonic probe for examining a specimen. The ultrasonic probe includes a holding portion, an insertion member, and an ultrasonic generator. The holding portion includes a first housing portion. The insertion member is configured to move along the first housing portion. The insertion member has at least one end for insertion into an endocavity of the specimen. The ultrasonic generator is provided at the one end of the insertion member and configured to transmit an ultrasound pulse to the specimen and collect an echo signal resulting from the transmitted ultrasound pulse.

According to the second aspect of the present invention, there is provided an ultrasound imaging apparatus for obtaining and displaying an ultrasound image. The apparatus includes an ultrasonic probe for examining a specimen and a display. The ultrasonic probe includes a holding portion, an insertion member, and an ultrasonic generator. The holding portion includes a first housing portion. The insertion member is configured to move along the first housing portion. The insertion member has at least one end for insertion into an endocavity of the specimen. The ultrasonic generator is provided at the one end of the insertion member and configured to transmit an ultrasound pulse to the specimen and collect an echo signal resulting from the transmitted ultrasound pulse. The display is coupled to the ultrasonic probe and configured to display the ultrasound image based on the echo signal.

According to the third aspect of the present invention, there is provided a method of providing an ultrasound image. The method begins by providing a holding portion having a housing portion. The method continues by providing an insertion member having a distal end and a proximal end. The distal end has an ultrasonic generator. The method further continues by slidably coupling the insertion member to the housing portion of the holding portion.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DESCRIPTION OF THE PREFERRED EMBODIMENTS

Embodiments of the present invention will be described with reference to the accompanying drawings.

First Embodiment

Figure 4A:
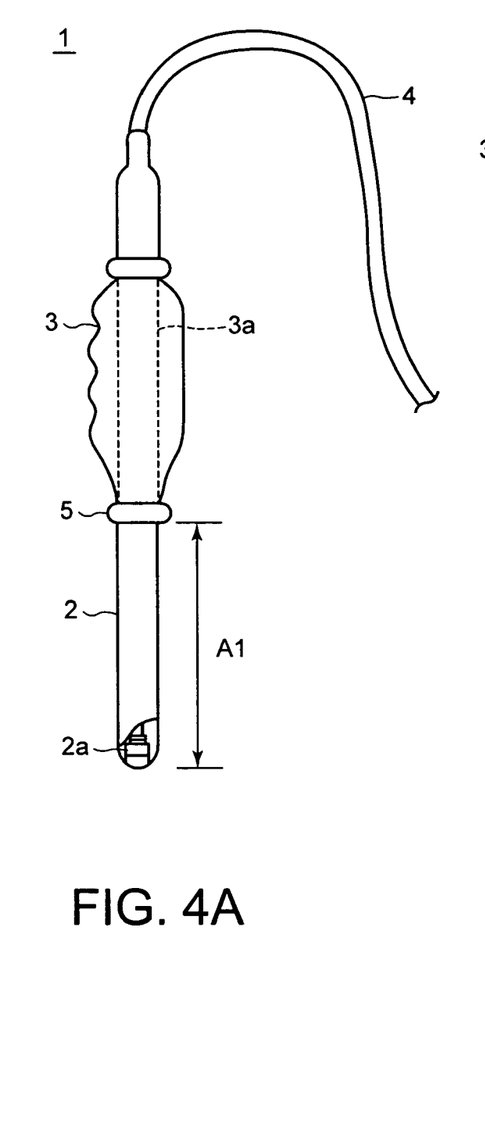
FIGS. 4A and 4B are illustrations showing an exemplary configuration of an ultrasonic probe according to the first embodiment of the present invention.
Figure 4B:
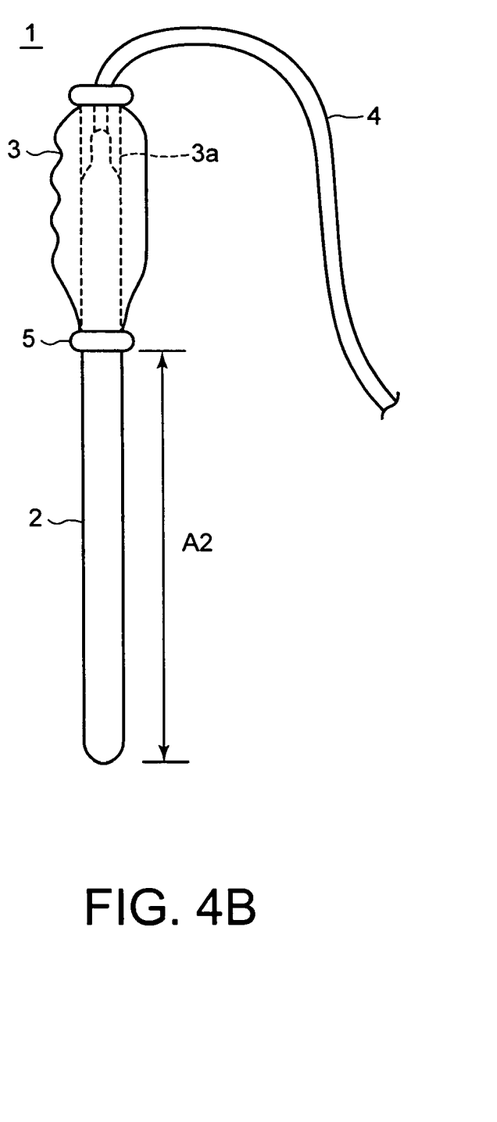

FIGS. 4A and 4B are illustrations showing an exemplary configuration of an ultrasonic probe according to the first embodiment of the present invention. As shown in FIG. 4A, an endocavity probe 1 is used as an example of the ultrasonic probe according to the first embodiment of the present invention. The endocavity probe 1 includes an insertion rod (as an example of an insertion member) 2, a handgrip (as an example of a holding portion) 3, a cable 4, and a fixer (or a fastener) 5. The insertion rod 2 includes an ultrasonic sensor 2a at its head (distal) end and is inserted into an endocavity of a specimen such as a patient P or an abject to be examined. The abdominal cavity is one example of an endocavity of the patient P. In one embodiment, the insertion rod 2 is sufficiently thin so as to reduce an incision size for the insertion of the insertion rod 2 in the abdominal cavity. This may help reduce patient's discomfort associated with the insertion. The ultrasonic sensor 2a typically includes a plurality of transducers which contact with a body of the patient P in use and repeatedly transmit ultrasound pulses to the body. The transmitted ultrasound pulses return to the transducers as ultrasound echo signals. The echo signals are collected by the transducers. The transducers also transmit the ultrasound pulses indifferent directions and can adjust the transmission direction during the transmission so that a predetermined area of the body can be scanned. During the scanning, the transducers collect echo signal information resulting from the transmitted pulses in the body of the patient P. Ultrasound images are displayed based on the collected information in an ultrasound imaging apparatus such as an ultrasound diagnosis apparatus (not shown in FIG. 4A). The ultrasonic sensor 2a is connected to a main unit (not shown in FIG. 4A) of the ultrasound diagnosis apparatus through the cable 4. Although the one embodiment described above of the ultrasonic sensor 2a is explained herein, the ultrasonic sensor 2a can be any type of sensor suitable for an ultrasound imaging.

The handgrip 3 is used to handle (or manipulate) the insertion rod 2 during the examination. In one embodiment, the handgrip 3 includes a housing 3a through which the insertion rod 2 passes. That is, the insertion rod 2 can be moved back and forth in the housing 3a along a longitudinal direction of the handgrip 3. Or in other words, the handgrip 3 can be moved back and forth or slid along the insertion rod 2. The housing 3a may provide a hole through which the insertion rod 2 passes in the longitudinal direction of the handgrip 3. Alternatively, the housing 3a may provide a groove through which the insertion rod 2 passes in the longitudinal direction of the handgrip 3. A form provided by the housing 3a is not limited to the above examples, but may be any other form which allows changing a relative position between the handgrip 3 and the insertion rod 2. By moving the handgrip 3 relative to the insertion rod 2, the length between the ultrasonic sensor 2a and the fixer 5 is changed as shown in FIG. 4B. The handgrip 3 may have a shape and size which makes it easy for the operator Q to handle the handgrip 3. The handgrip 3 can be fixed to the insertion rod 2 at a desired position by the fixer 5. It can alternatively be understood that the insertion rod 2 is fixed to the handgrip 3 at a desired position by the fixer 5.

It may be possible to fix the length between the ultrasonic sensor 2a and the bottom of the handgrip 3 without the fixer 5. For example, the handgrip 3 is divided into two pieces, and the divided pieces are attached to each other. When one or both of the divided pieces have a concavity (concavities) and the insertion rod 2 has a plurality of convexities along its longitudinal direction, the divided pieces are attached to the insertion rod 2 in a manner that the concavity is attached to one of the convexities. Alternatively, when one or both of the divided pieces have a convexity (convexities) and the insertion rod 2 has a plurality of concavities along its longitudinal direction, the divided pieces are attached to the insertion rod 2 in a manner that the convexity is attached to one of the concavities.

With the above configuration, when the endocavity probe 1 is applied to a shallow part from the abdominal wall of the patient P, the length of the insertion rod 2 between the ultrasonic sensor 2a and the fixer 5 is shortened by moving the handgrip 3 towards the ultrasonic sensor 2a, relative to the insertion rod 2, or by moving the insertion rod 2 towards the cable 4, relative to the handgrip 3, as shown in FIG. 4A. When a desired length A1 is determined, the position for the length A1 is kept by the fixer 5 as shown in FIG. 4A. The length A1 depends on application cases, but may be, for example, 100 to 150 millimeters.

As shown in FIG. 4B, when the endocavity probe 1 is applied to a deep part from the abdominal wall of the patient P, the insertion rod 2 is lengthened by moving the handgrip 3 towards the cable 4, relative to the insertion rod 2, or by moving the insertion rod 2 towards the ultrasonic sensor 2a, relative to the handgrip 3, as shown in FIG. 4B. When a desired length A2 is determined, the position for the length A2 is kept by the fixer 5 as shown in FIG. 4B. The length A2 depends on application cases, but may be, for example, 300 to 450 millimeters.

Figure 5A:
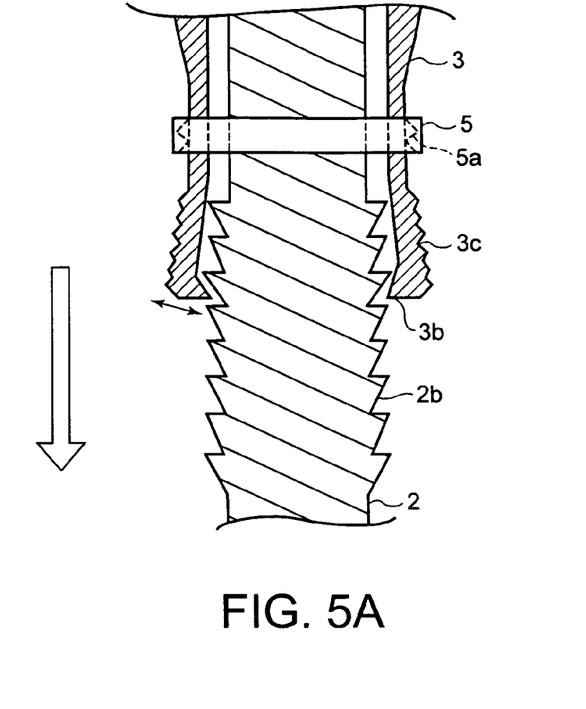
FIGS. 5A and 5B are illustrations showing an example of a fixing configuration according to the first embodiment of the present invention.
Figure 5B:
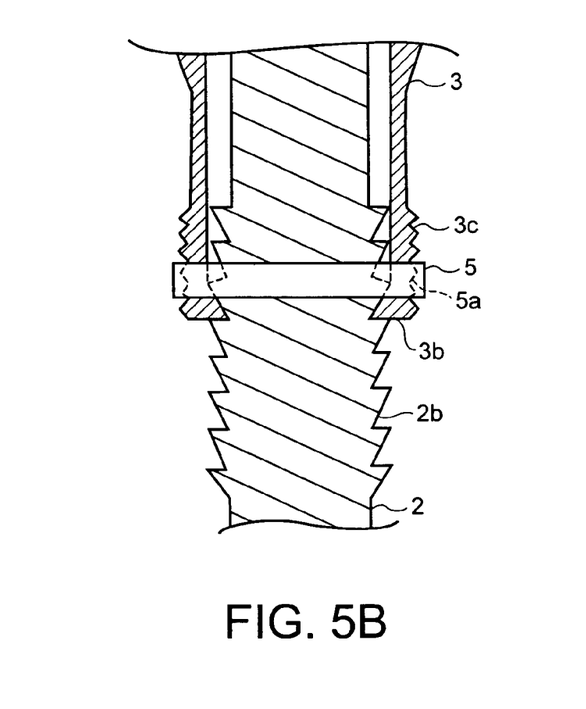

A fixing configuration using the fixer 5 will be described with reference to FIGS. 5A and 5B. FIG. 5A is an illustration showing an example of the fixing configuration when released according to the first embodiment of the present invention. FIG. 5B is an illustration showing an example of the fixing configuration when fixed according to the first embodiment of the present invention.

As shown in FIG. 5A, a plurality of projections 2b are provided around a surface of the insertion rod 2. In one embodiment, the projections 2b are formed of a saw-tooth appearance along the longitudinal direction of the insertion rod 2. The saw tooth appearance forms an acute angle slanted towards the ultrasonic sensor 2a. The projections 2b are used for the fixation of the handgrip 3 and the insertion rod 2 relative to each other. At an internal side of the bottom end of the handgrip 3, a projection 3b is provided in an unguiform as shown in FIG. 5A so as to avoid the insertion rod 2 from moving towards the cable 4, relative to the handgrip 3. Further, an outside of the bottom end of the handgrip 3 is formed of a thread profile 3c. Another thread profile 5a formed in an internal side of the fixer 5 can be engaged with the thread profile 3c.

With the above configuration, the thread profiles 3c and 5a are not engaged in a released status in FIG. 5A. Accordingly, the projection 3b of the handgrip 3 is released from the projections 2b of the insertion rod 2. As a result, the insertion rod 2 can be moved through the housing 3a of the handgrip 3. In other words, the handgrip 3 can be moved along the insertion rod 2.

As shown in FIG. 5B, when the length A1 (or A2) of the insertion rod 2 has been adjusted to a preferred length according to, for example, the depth between the abdominal wall and the object (organ or tissues) which contacts with the ultrasonic sensor 2a, the fixer 5 is moved towards the thread profile 3c and rotated so as to engage the thread profile 3c of the handgrip 3 and the thread profile 5a of the fixer 5. When the fixer 5 is rotated down towards the bottom end of the handgrip 3, the projection 3b is engaged with one of the projections 2b. Accordingly, the insertion rod 2 and the handgrip 3 are fixed to each other.

The projections 2b are provided in a predetermined range along the longitudinal direction of the insertion rod 2, for example, up from a position of 20 to 30 millimeters from the bottom of the insertion rod 2.

The thread profile relationship described above is only one example of the fixer 5. A use of a screw or a pin, or any other possible fixation configuration may be applied to the endocavity probe 1 according to the first embodiment of the present invention.

After the use of the endocavity probe 1, that is, after the insertion rod 2 has been pulled out from an endocavity, it is usually necessary to sterilize the endocavity probe 1. Prior to sterilizing the endocavity probe 1, the endocavity probe 1 may be disassembled to the insertion rod 2, the handgrip 3, and the fixer 5. The insertion rod 2 can be pulled out from the handgrip 3. Or the handgrip 3 can be pulled out from the insertion rod 2. The fixer 5 can be pulled out or detached from the handgrip 3. Each disassembled component may be soaked in predetermined disinfectant liquid for the sterilization. For the sterilization, each component of the endocavity probe 1 may be made of materials used for a conventional endocavity probe. One example of the materials may be plastic. A processing may be conducted on the inside of the insertion rod 2 for the purpose of waterproof and operational stability of the endocavity probe 1. Such processing is, for example, made by a mold processing.

As described above, in the endocavity probe 1 according to the first embodiment, the handgrip 3 can be moved and fixed by the fixer 5 at a desired position of the insertion rod 2 so as to adjust the length of the insertion rod 2 between the ultrasonic sensor 2a and the fixer 5. Therefore, the length of the insertion rod 2 between the ultrasonic sensor 2a and the fixer 5 is freely adjusted to a desired or preferred length in accordance with an examination, types of laparoscopy or the depth between the abdominal wall and the object which contacts with the ultrasonic sensor 2a. The endocavity probe 1 may be used without the conventional problem even when the object such as tissues or an organ is at a shallow part from the abdominal wall of the patient P. Also, the endocavity probe 1 may easily be handled by adjusting the length when the laparoscopy is conducted without a trocar. The operator Q may also have a similar handling in the use of the endocavity probe 1 to a conventional endocavity probe when the trocar is used or when the object is at a deep part from the abdominal wall of the patient P.

Second Embodiment

Figure 6A:
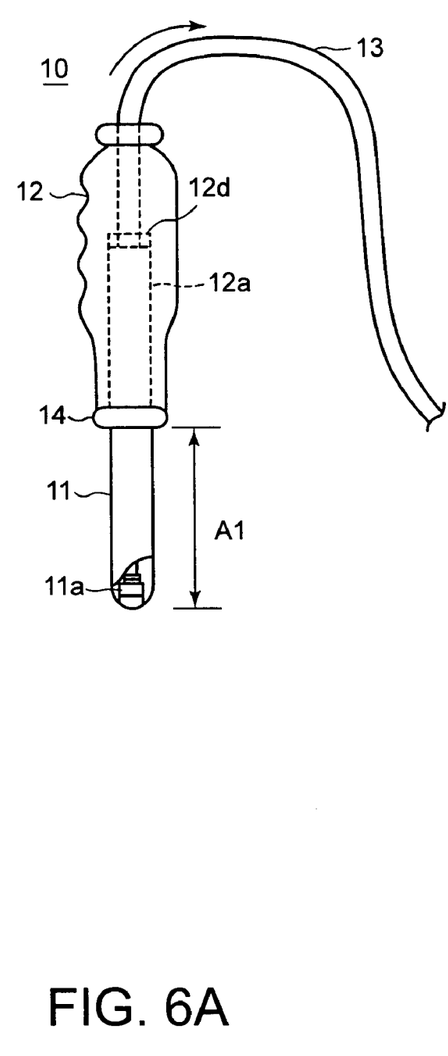
FIGS. 6A and 6B are illustrations showing an exemplary configuration of the ultrasonic probe according to the second embodiment of the present invention.
Figure 6B:
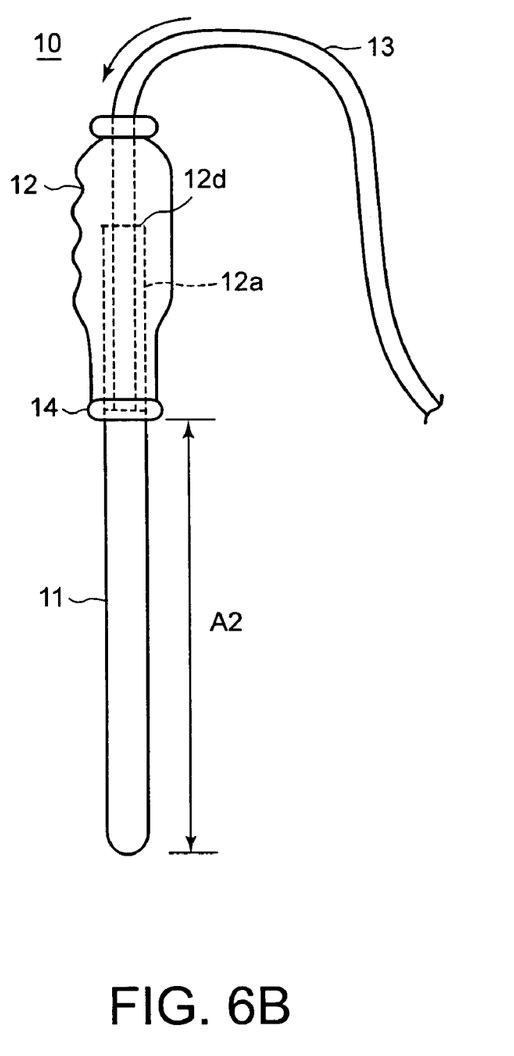

FIGS. 6A and 6B are illustrations showing an exemplary configuration of an ultrasonic probe according to the second embodiment of the present invention. As shown in FIG. 6A, an endocavity probe 10 is used as an example of the ultrasonic probe according to the second embodiment of the present invention. The endocavity probe 10 includes an insertion rod (as an example of an insertion member) 11, a handgrip (as an example of a holding portion) 12, a cable 13, and a fixer (or a fastener) 14. The insertion rod 11 includes an ultrasonic sensor 11a at its head (distal) end and is inserted into an endocavity of the patient P. The abdominal cavity is one example part of an endocavity of the patient P. In one embodiment, the insertion rod 11 is sufficiently thin so as to reduce an incision size for the insertion of the insertion rod 11 in the abdominal cavity. This may help reduce patient's discomfort associated with the insertion. The ultrasonic sensor 11a typically includes a plurality of transducers which contact with a body of the patient P in use and repeatedly transmit ultrasound pulses to the body. The transmitted ultrasound pulses return to the transducers as ultrasound echo signals. The echo signals are collected by the transducers. The transducers also transmit the ultrasound pulses in different directions and can adjust the transmission direction during the transmission so that a predetermined area of the body can be scanned. During the scanning, the transducers collect echo signal information resulting from the transmitted pulses in the body of the patient P. Ultrasound images are displayed based on the collected information in an ultrasound imaging apparatus such as an ultrasound diagnosis apparatus (not shown in FIG. 6A). The ultrasonic sensor 11a is connected to a main unit (not shown in FIG. 6A) of the ultrasound diagnosis apparatus through the cable 13. Although the one embodiment described above of the ultra sonic sensor 11a is explained herein, the ultrasonic sensor 11a can be any type of sensor suitable for an ultrasound imaging.

The handgrip 12 is used to handle (or manipulate) the insertion rod 11 during the examination. In one embodiment, the handgrip 12 includes a housing 12a which one end side of the insertion rod 11 is slid in and out from. The end side is opposite to another end side where the ultrasonic sensor 11a is provided. That is, the insertion rod 11 can be inserted in and pulled out from the housing 12a. Only one end of the handgrip 12 has an opening for the housing for insertion of the insertion rod 11, and the handgrip 12 has a rod stopping portion 12d for preventing the insertion rod 11 from moving through the handgrip 12. Accordingly, the insertion rod 11 does not slide through the handgrip 12. The housing 12a may provide a hole which the insertion rod 11 slides in and out from in the longitudinal direction of the handgrip 12. Alternatively, the housing 12a may provide a groove which the insertion rod 11 slides in and out from in the longitudinal direction of the handgrip 12. A form provided by the housing 12a is not limited to the above examples, but may be any other form which allows changing a relative position between the handgrip 12 and the insertion rod 11. By moving the insertion rod 11 relative to the handgrip 12, the length between the ultrasonic sensor 11a and the fixer 14 is changed as shown in FIGS. 6A and 6B. The handgrip 12 may have a shape and size which makes it easy for the operator Q to handle the handgrip 12. The insertion rod 11 can be fixed to the handgrip 12 at a desired position by the fixer 14.

With the above configuration, when the endocavity probe 10 is applied to a shallow part from the abdominal wall of the patient P, the length of the insertion rod 11 between the ultrasonic sensor 11a and the fixer 14 is shortened by inserting the insertion rod 11 into the housing 12a as shown in FIG. 6A. When the insertion rod 11 is inserted into the housing 12a, the cable 13 is pushed out from the handgrip 12 (the housing 12a) in the direction shown by the arrowhead in FIG. 6A. When a desired length A1 is determined, the position for the length A1 is kept by the fixer 14 as shown in FIG. 6A. The length A1 depends on application cases, but may be, for example, 100 to 150 millimeters.

As shown in FIG. 6B, when the endocavity probe 10 is applied to a deep part from the abdominal wall of the patient P, the insertion rod 11 is lengthened by pulling out the insertion rod 11 from the housing 12a as shown in FIG. 6B. When the insertion rod 11 is pulled out from the housing 12a, the cable 13 is brought into the handgrip 12 (the housing 12a) in the direction shown by the arrowhead in FIG. 6B. When a desired length A2 is determined, the position for the length A2 is kept by the fixer 14 as shown in FIG. 6B. The length A2 depends on application cases, but may be, for example, 300 to 450 millimeters.

Figure 7A:
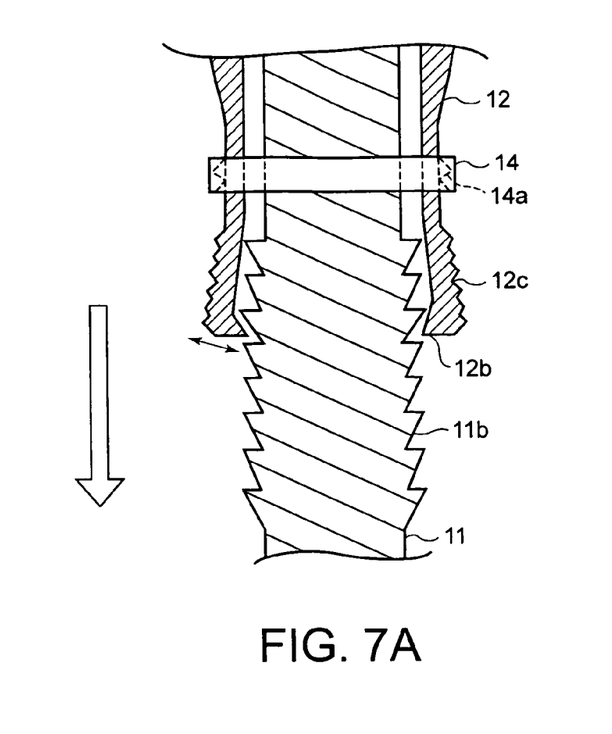
FIGS. 7A and 7B are illustrations showing an example of the fixing configuration according to the second embodiment of the present invention.
Figure 7B:
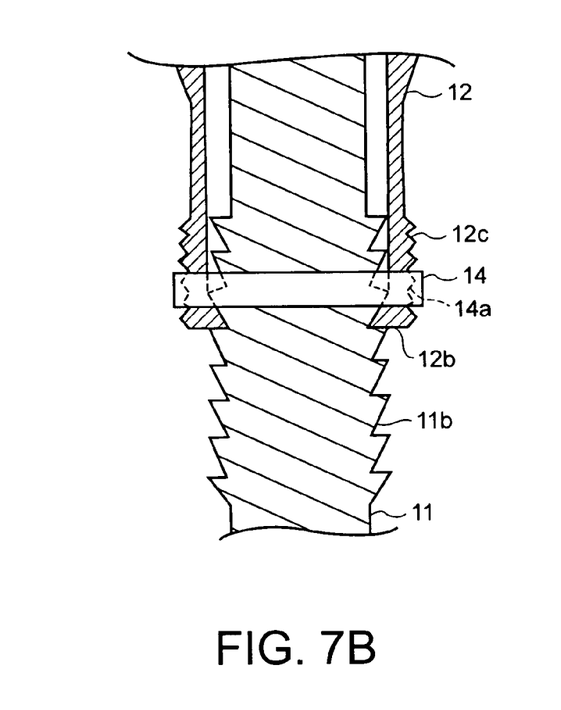

A fixing configuration using the fixer 14 will be described with reference to FIGS. 7A and 7B. FIG. 7A is an illustration showing an example of the fixing configuration when released according to the second embodiment of the present invention. FIG. 7B is an illustration showing an example of the fixing configuration when fixed according to the second embodiment of the present invention.

As shown in FIG. 7A, a plurality of projections 11b are provided around a surface of the insertion rod 11. In one embodiment, the projections 11b are formed of a saw-tooth appearance along the longitudinal direction of the insertion rod 11. The saw tooth appearance forms an acute angle slanted towards the ultrasonic sensor 11a. The projections 11b are used for the fixation of the handgrip 12 and the insertion rod 11 relative to each other. At an internal side of the bottom end of the handgrip 12, a projection 12b is provided in an unguiform as shown in FIG. 7A so as to avoid the insertion rod 11 from moving towards the cable 13, relative to the handgrip 12. Further, an outside of the bottom end of the handgrip 12 is formed of a thread profile 12c. Another thread profile 14a formed in an internal side of the fixer 14 can be engaged with the thread profile 12c.

With the above configuration, the thread profiles 12c and 14a are not engaged in the released status in FIG. 7A. Accordingly, the projection 12b of the handgrip 12 is released from the projections 11b of the insertion rod 11. As a result, the insertion rod 11 can be slid in and out from the housing 12a of the handgrip 12.

As shown in FIG. 7B, when the length A1 (or A2) of the insertion rod 11 has been adjusted to a preferred length according to, for example, the depth between the abdominal wall and the object (organ or tissues) which contacts with the ultrasonic sensor 11a, the fixer 14 is moved towards the thread profile 12c and rotated so as to engage the thread profile 12c of the handgrip 12 and the thread profile 14a of the fixer 14. When the fixer 14 is rotated down towards the bottom end of the handgrip 12, the projection 12b is engaged with one of the projections 11b. Accordingly, the insertion rod 11 and the handgrip 12 are fixed to each other.

The projections 11b are provided in a predetermined range along the longitudinal direction of the insertion rod 11, for example, up from a position of 20 to 30 millimeters from the bottom of the insertion rod 11.

The thread profile relationship described above is only one example of the fixer 14. A use of a screw or a pin, or any other possible fixation configuration may be applied to the endocavity probe 10 according to the second embodiment of the present invention.

After the use of the endocavity probe 10, that is, after the insertion rod 11 has been pulled out from an endocavity, it is usually necessary to sterilize the endocavity probe 10. Prior to sterilizing the endocavity probe 10, the endocavity probe 10 may be disassembled to the insertion rod 11, the handgrip 12, and the fixer 14. The insertion rod 11 can be pulled out from the handgrip 12. The fixer 14 can be pulled out or detached from the handgrip 12. Each disassembled component may be soaked in predetermined disinfectant liquid for the sterilization. For the sterilization, each component of the endocavity probe 10 may be made of materials used for a conventional endocavity probe. One example of the materials may be plastic. A processing may be conducted on the inside of the insertion rod 11 for the purpose of waterproof and operational stability of the endocavity probe 10. Such processing is, for example, made by a mold processing.

As described above, in the endocavity probe 10 according to the second embodiment, the insertion rod 11 can be moved and fixed by the fixer 14 at a desired position of the insertion rod 11 so as to adjust the length of the insertion rod 11 between the ultrasonic sensor 11a and the fixer 14. Therefore, the length of the insertion rod 11 between the ultrasonic sensor 11a and the fixer 14 is freely adjusted to a desired or preferred length in accordance with an examination, types of laparoscopy or the depth between the abdominal wall and the object which contacts with the ultrasonic sensor 11a. The endocavity probe 10 may be used without the conventional problem even when the object such as tissues or an organ is at a shallow part from the abdominal wall of the patient P. Also, the endocavity probe 10 may easily be handled by adjusting the length when the laparoscopy is conducted without a trocar. The operator Q may also have a similar handling in the use of the endocavity probe 10 to a conventional endocavity probe when the trocar is used or when the object is at a deep part from the abdominal wall of the patient P.

Third Embodiment

Figure 8A:
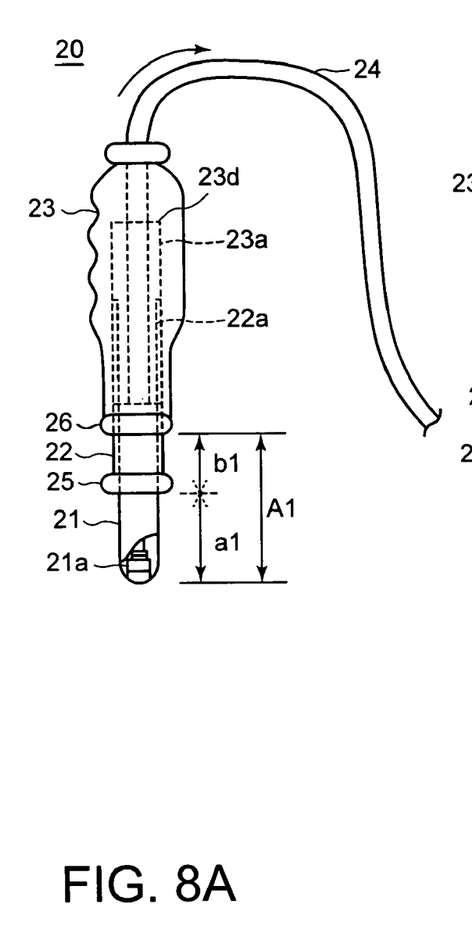
FIGS. 8A and 8B are illustrations showing an exemplary configuration of the ultrasonic probe according to the third embodiment of the present invention.
Figure 8B:
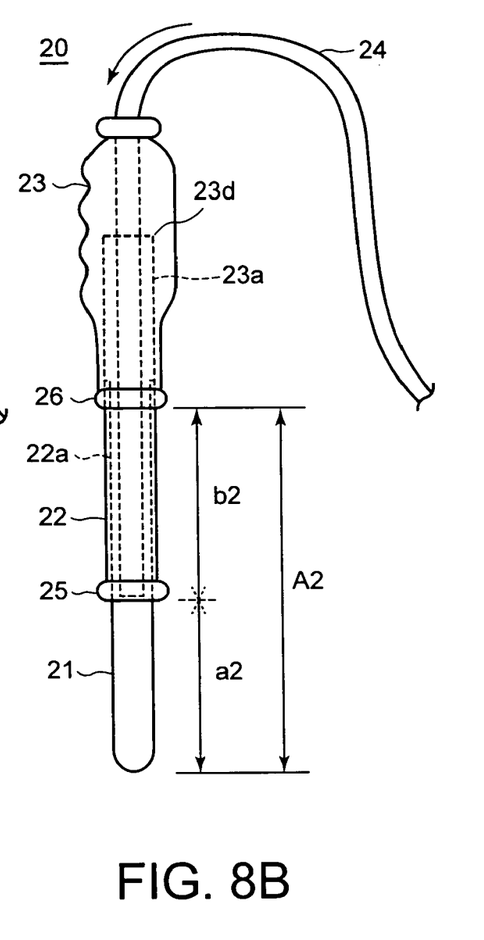

FIGS. 8A and 8B are illustrations showing an exemplary configuration of an ultrasonic probe according to the third embodiment of the present invention. As shown in FIG. 8A, an endocavity probe 20 is used as an example of the ultrasonic probe according to the third embodiment of the present invention. The endocavity probe 20 includes an insertion end rod (as an example of an insertion end member) 21, a relay rod (as an example of a relay member) 22, a handgrip (as an example of a holding portion) 23, a cable 24, and fixers (or fasteners) 25 and 26.

The insertion end rod 21 includes an ultrasonic sensor 21a at its head (distal) end and is inserted into an endocavity of the patient P. The abdominal cavity is one example part of an endocavity of the patient P. In one embodiment, the insertion end rod 21 is sufficiently thin so as to reduce an incision size for the insertion of the insertion end rod 21 in the abdominal cavity. This may help reduce patient's discomfort associated with the insertion. The ultrasonic sensor 21*a* typically includes a plurality of transducers which contact with a body of the patient P in use and repeatedly transmit ultrasound pulses to the body. The transmitted ultrasound pulses return to the transducers as ultrasound echo signals. The echo signals are collected by the transducers. The transducers also transmit the ultrasound pulses indifferent directions and can adjust the transmission direction during the transmission so that a predetermined area of the body can be scanned. During the scanning, the transducers collect echo signal information resulting from the transmitted pulses in the body of the patient P. Ultrasound images are displayed based on the collected information in an ultrasound imaging apparatus such as an ultrasound diagnosis apparatus (not shown in FIG. 8A). The ultrasonic sensor 21*a* is connected to a main unit (not shown in FIG. 8A) of the ultrasound diagnosis apparatus through the cable 24. Although the one embodiment described above of the ultra sonic sensor 21*a* is explained herein, the ultrasonic sensor 21*a* can be any type of sensor suitable for an ultrasound imaging.

In one embodiment, the relay rod 22 includes a housing 22*a* which one end side of the insertion end rod 21 is slid in and out from. The end side is opposite to another end side where the ultrasonic sensor 21*a* is provided. That is, the insertion end rod 21 can be inserted in and pulled out from the housing 22*a*. By moving the insertion end rod 21 relative to the relay rod 22, the length between the ultrasonic sensor 21*a* and the bottom end of the relay rod 22 where the fixer 25 is applied is changed as shown in FIGS. 8A and 8B. The insertion end rod 21 is fixed to the relay rod 22 at a desired position by the fixer 25. The relay rod 22 is also sufficiently thin so as to reduce an incision size for the insertion of the insertion end rod 21 in the abdominal cavity. This may help reduce patient's discomfort associated with the insertion. The housing 22*a* may provide a hole which the insertion end rod 21 slides in and out from in the longitudinal direction of the relay rod 22. Alternatively, the housing 22*a* may provide a groove which the insertion end rod 21 slides in and out from in the longitudinal direction of the relay rod 22. A form provided by the housing 22*a* is not limited to the above examples, but may be any other form which allows changing a relative position between the relay rod 22 and the insertion end rod 21. The insertion end rod 21 and the relay rod 22 are assembled in a telescopic manner and form an insertion rod (or an insertion member).

The handgrip 23 is used to handle (or manipulate) the insertion rod during the examination. In one embodiment, the handgrip 23 includes a housing 23*a* which one end side of the relay rod 22 is slid in and out from. The end side is opposite to another end side where the insertion end rod 21 is inserted. That is, the relay rod 22 can be inserted in and pulled out from the housing 23*a*. Only one end of the handgrip 23 has an opening for the housing for insertion of the relay rod 22, and the handgrip 23 has a rod stopping portion 23*d* for preventing the relay rod 22 (the insertion rod) from moving through the handgrip 23. Accordingly, the relay rod 22 (the insertion rod) does not slide through the handgrip 23. The housing 23*a* may provide a hole which the relay rod 22 slides in and out from in the longitudinal direction of the handgrip 23. Alternatively, the housing 23*a* may provide a groove which the relay rod 22 slides in and out from in the longitudinal direction of the handgrip 23. A form provided by the housing 23*a* is not limited to the above examples, but may be any other form which allows changing a relative position between the handgrip 23 and the relay rod 22. By moving the relay rod 22 relative to the handgrip 23, the length between the bottom end of the relay rod 22 and the bottom end of the handgrip 23 where the fixer 26 is applied is changed as shown in FIGS. 8A and 8B. The handgrip 23 may have a shape and size which makes it easy for the operator Q to handle the handgrip 23. The relay rod 22 can be fixed to the handgrip 23 at a desired position by the fixer 26.

With the above configuration, when the endocavity probe 20 is applied to a shallow part from the abdominal wall of the patient P, the length of the insertion rod between the ultrasonic sensor 21*a* and the fixer 26 is shortened by inserting both the insertion end rod 21 into the housing 22*a* and the relay rod 22 into the housing 23*a* as shown in FIG. 8A. Alternatively, only the insertion end rod 21 may be inserted into the housing 22*a* or only the relay rod 22 may be inserted into the housing 23*a*. When the insertion rod is shortened, the cable 24 is pushed out from the handgrip 23 (the housing 23*a*) in the direction shown by the arrowhead in FIG. 8A. When a desired length A1 (=a1+b1) is determined, the positions of the insertion end rod 21 and the relay rod 22 for the lengths a1 and b1 are kept by the fixers 25 and 26 as shown in FIG. 8A. The length A1 depends on application cases, but may be, for example, 100 to 150 millimeters.

As shown in FIG. 8B, when the endocavity probe 20 is applied to a deep part from the abdominal wall of the patient P, the insertion rod is lengthened by pulling out both the insertion end rod 21 from the housing 22*a* and the relay rod 22 from the housing 23*a* as shown in FIG. 8B. Alternatively, only the insertion end rod 21 may be pulled out from the housing 22*a* or only the relay rod 22 may be pulled out from the housing 23*a*. When the insertion rod is lengthened, the cable 24 is brought into the handgrip 23 (the housing 23*a*) in the direction shown by the arrowhead in FIG. 8B. When a desired length A2 (=a2+b2) is determined, the positions of the insertion end rod 21 and the relay rod 22 for the lengths a2 and b2 are kept by the fixers 25 and 26 as shown in FIG. 8B. The length A2 depends on application cases, but may be, for example, 300 to 450 millimeters.

Figure 9A:
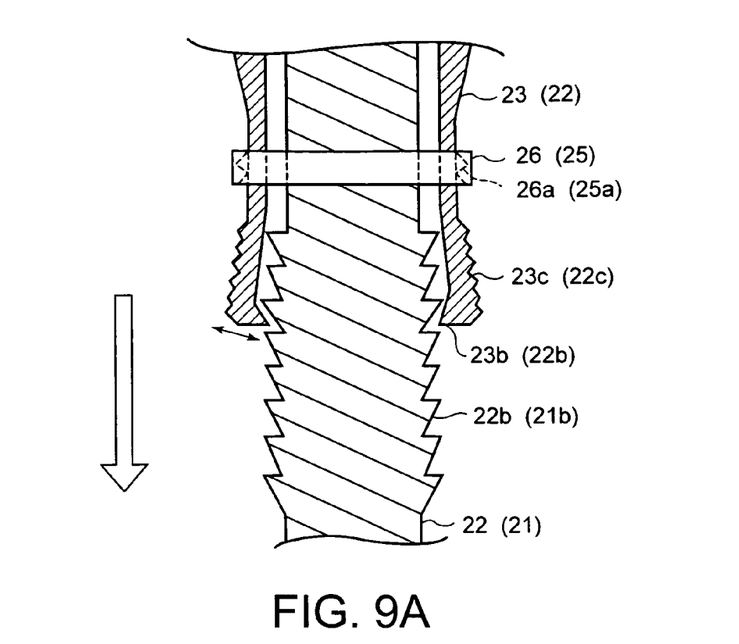
FIGS. 9A and 9B are illustrations showing an example of the fixing configurations according to the third embodiment of the present invention.
Figure 9B:
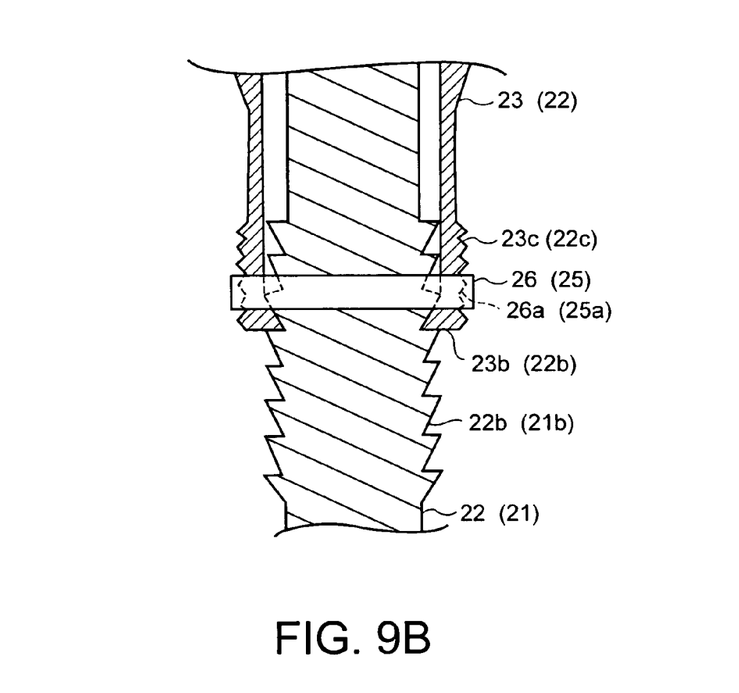

Fixing configurations using the fixers 25 and 26 will be described with reference to FIGS. 9A and 9B. FIG. 9A is an illustration showing an example of the fixing configurations when released according to the third embodiment of the present invention. FIG. 9B is an illustration showing an example of the fixing configurations when fixed according to the third embodiment of the present invention. Since the fixing configuration using the fixer 25 is similar to the fixing configuration using the fixer 26, explanations with respect to the fixing configuration using the fixer 25 will be omitted but corresponding parts names and reference numbers will be added in parentheses. Also in FIGS. 9A and 9B, the corresponding pars reference numbers are added in parentheses.

As shown in FIG. 9A, a plurality of projections 22*b* (projections 21*b*) are provided around a surface of the relay rod 22 (insertion end rod 21). In one embodiment, the projections 22*b* (projections 21*b*) are formed of a saw-tooth appearance along the longitudinal direction of the relay rod 22 (insertion end rod 21). The saw tooth appearance forms an acute angle slanted towards the ultrasonic sensor 21*a*. The projections 22*b* (projections 21*b*) are used for the fixation of the handgrip 23 (relay rod 22) and the relay rod 22 (insertion end rod 21) relative to each other. At an internal side of the bottom end of the handgrip 23 (relay rod 22), a projection 23*b* (projection 22*b*) is provided in an unguiform as shown in FIG. 9A so as to avoid the relay rod 22 (insertion end rod 21) from moving towards the cable 24, relative to the handgrip 23 (relay rod 22). Further, an outside of the bottom end of the handgrip 23 (relay rod 22) is formed of a thread profile 23*c* (thread profile 22c). Another thread profile 26a (thread profile 25a) formed in an internal side of the fixer 26 (fixer 25) can be engaged with the thread profile 23c (thread profile 22c).

With the above configuration, the thread profiles 23c and 26a (thread profiles 22c and 25a) are not engaged in the released status in FIG. 9A. Accordingly, the projection 23b (projection 22b) of the handgrip 23 (relay rod 22) is released from the projections 22b (projections 21b) of the relay rod 22 (insertion end rod 21). As a result, the relay rod 22 (insertion end rod 21) can be slid in and out from the housing 23a (housing 22a) of the handgrip 23 (relay rod 22).

As shown in FIG. 9B, when the length A1 (or A2) of the insertion rod has been adjusted to a preferred length according to, for example, the depth between the abdominal wall and the object (organ or tissues) which contacts with the ultrasonic sensor 21a, the fixer 26 (fixer 25) is moved towards the thread profile 23c (thread profile 22c) and rotated so as to engage the thread profile 23c of the handgrip 23 and the thread profile 26a of the fixer 26 (thread profiles 22c and 25a). When the fixer 26 (fixer 25) is rotated down towards the bottom end of the handgrip 23 (relay rod 22), the projection 23b (projection 22b) is engaged with one of the projections 22b (projections 21b). Accordingly, the relay rod 22 (insertion end rod 21) and the handgrip 23 (relay rod 22) are fixed to each other.

The projections 21b are provided in a predetermined range along the longitudinal direction of the insertion end rod 21, for example, up from a position of 20 to 30 millimeters from the bottom of the insertion end rod 21.

The thread profile relationship described above is only one example of the fixers 25 and 26. A use of a screw or a pin, or any other possible fixation configuration may be applied to the endocavity probe 10 according to the third embodiment of the present invention.

After the use of the endocavity probe 20, that is, after the insertion rod has been pulled out from an endocavity, it is usually necessary to sterilize the endocavity probe 20. Prior to sterilizing the endocavity probe 20, the endocavity probe 20 may be disassembled to the insertion end rod 21, the relay rod 22, the handgrip 23, and the fixers 25 and 26. The insertion end rod 21 can be pulled out from the relay rod 22. The fixer 25 can be pulled out or detached from the relay rod 22. The relay rod 22 can be pulled out from the handgrip 23. The fixer 26 can be pulled out or detached from the handgrip 23. Each disassembled component may be soaked in predetermined disinfectant liquid for the sterilization. For the sterilization, each component of the endocavity probe 20 may be made of materials used for a conventional endocavity probe. One example of the materials may be plastic. A processing may be conducted on the inside of the insertion end rod 21 for the purpose of waterproof and operational stability of the endocavity probe 20. Such processing is, for example, made by a mold processing.

As described above, in the endocavity probe 20 according to the third embodiment, the insertion end rod 21 and the relay rod 22 can be moved and fixed by the fixers 25 and 26 at desired positions of the insertion end rod 21 and the relay rod 22, respectively, so as to adjust the length of the insertion rod between the ultrasonic sensor 21a and the fixer 26. Therefore, the length of the insertion rod between the ultrasonic sensor 21a and the fixer 26 is freely adjusted to a desired or preferred length in accordance with an examination, types of laparoscopy or the depth between the abdominal wall and the object which contacts with the ultrasonic sensor 21a. The endocavity probe 20 may be used without the conventional problem even when the object such as tissues or an organ is at a shallow part from the abdominal wall of the patient P. Also, the endocavity probe 20 may easily be handled by adjusting the length when the laparoscopy is conducted without a trocar. The operator Q may also have a similar handling in the use of the endocavity probe 20 to a conventional endocavity probe when the trocar is used or when the object is at a deep part from the abdominal wall of the patient P.

According to the third embodiment, the insertion end rod 21 is inserted into the housing 22a of the relay rod 22, which is inserted into the housing 23a of the handgrip 23. Therefore, the size of the endocavity probe 20 is reduced. For some applications, the operator Q may handle the endocavity probe 20 more easily than the endocavity probe 1 according to the first embodiment or the endocavity probe 10 according to the second embodiment. The endocavity probe 20 may also be made in a reduced size, compared to the endocavity probe 1 according to the first embodiment or the endocavity probe 10 according to the second embodiment. In the embodiment shown in FIG. 8A, only one relay rod 22 is used. However, a plurality of relay rods may be used.

In the embodiments of the present invention, the endocavity probe may have an ultrasonic sensor whose transducers' transmission direction is changeable so as to transmit ultrasound pulses in various directions. For example, the transducers may transmit the ultrasound pulses in a direction perpendicular to the longitudinal direction of the insertion rod. In this example, the ultrasonic sensor may be contacted to a side of an object such as an organ or tissues in the body of the patient P.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the invention may be practiced otherwise than as specifically described herein.

The invention claimed is:

1. An ultrasonic probe for insertion into an endocavity of a specimen in order to examine the specimen, comprising:
   a holding portion including a first housing portion;
   an insertion member configured to move along the first housing portion in a longitudinal direction, the insertion member having at least one end for insertion into the endocavity of the specimen
   wherein said insertion member includes a plurality of projections extending along an outer surface of the insertion member and in the longitudinal direction, said holding portion including a clasp configured to engage and disengage with said plurality of projections, and an area of said holding portion including the clasp also including a first thread profile; an
   a fixer configured to move along said holding portion in the longitudinal direction so as to surround the clasp and the plurality of projections, the fixer including a second thread profile and the fixer being further configured to engage with the area of said holding portion including the first thread profile by coupling the second thread profile with the first thread profile; and an ultrasonic generator provided at the one end of the insertion member and configured to transmit an ultrasound pulse to the specimen and collect an echo signal resulting from the transmitted ultrasound pulse.

2. The ultrasonic probe according to claim 1, wherein the insertion member moves through the first housing portion.

3. The ultrasonic probe according to claim 1, wherein the first housing portion includes an insertion member stopping portion configured to prevent the insertion member from moving through the holding portion.

4. The ultrasonic probe according to claim 1, wherein the is configured to rotate about the holding portion.

5. The ultrasonic probe according to claim 1, wherein the insertion member includes a relay member having a second housing portion and an insertion end member having the one end, the relay member being configured to move along the first housing portion, the insertion end member being configured to move along the second housing portion.

6. The ultrasonic probe according to claim 5, further comprising another fixer disposed at the relay member and configured to keep the insertion end member and the relay member at a second predetermined position relative to each other.

7. The ultrasonic probe according to claim 5, wherein the first housing portion includes a relay member stopping portion configured to prevent the relay member from moving through the holding portion, and wherein the second housing portion includes an insertion end member stopping portion configured to prevent the insertion end member from moving through the relay member.

8. An ultrasound imaging apparatus for obtaining and displaying an ultrasound image, the apparatus comprising:
an ultrasonic probe for insertion into an endocavity of a specimen in order to examine the specimen, including
a holding portion including a first housing portion,
an insertion member configured to move along the first housing portion in a longitudinal direction, the insertion member having at least one end for insertion into the endocavity of the specimen,
wherein said insertion member includes a plurality of projections extending along an outer surface of the insertion member and in the longitudinal direction, said holding portion including a clasp configured to engage and disengage with said plurality of projections and an area of said holding portion including the clasp also including a first thread profile,
a fixer configured to move along said holding portion in the longitudinal direction so as to surround the clasp and the plurality of projections, the fixer including a second thread profile, and the fixer being further configured to engage with the area of said holding portion including the first thread profile by coupling the second thread profile with the first thread profile, and
an ultrasonic generator provided at the one end of the insertion member and configured to transmit an ultrasound pulse to the specimen and collect an echo signal resulting from the transmitted ultrasound pulse; and
a display coupled to the ultrasonic probe and configured to display the ultrasound image based on the echo signal.

9. A method of generating an ultrasound image, comprising:
providing a holding portion having a housing portion;
providing an insertion member having a distal end and a proximal end, the distal end having an ultrasonic generator,
wherein said insertion member includes,
a plurality of projections extending along an outer surface of the insertion member and in the longitudinal direction, said holding portion including a clasp configured to engage and disengage with said plurality of projections, and an area of said holding portion including the clasp also including a first thread profile, and
a fixer configured to move along said holding portion in the longitudinal direction so as to surround the clasp and the plurality of projections, the fixer including a second thread profile, and the fixer being further configured to engage with the area of said holding portion including the first thread profile by coupling the second thread profile with the first thread profile;
adjusting a position of the ultrasonic generator, which is coupled to the holding portion;
inserting the distal end of the insertion member into an endocavity of a specimen; and generating the ultrasound image.

* * * * *